United States Patent
Axén et al.

(10) Patent No.: US 7,025,824 B2
(45) Date of Patent: *Apr. 11, 2006

(54) CERAMIC MATERIAL AND PROCESS FOR MANUFACTURING

(75) Inventors: Niklas Axén, Järlåsa (SE); Leif Hermansson, Uppsala (SE); Tobias Persson, Uppsala (SE); Kajsa Björklund, Uppsala (SE); Lars Kraft, Uppsala (SE)

(73) Assignee: CerBio Tech AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/322,488

(22) Filed: Dec. 19, 2002

(65) Prior Publication Data
US 2004/0237847 A1   Dec. 2, 2004

(30) Foreign Application Priority Data
Dec. 27, 2001  (SE) .................................. 0104441-1

(51) Int. Cl.
*A61K 6/06*   (2006.01)

(52) U.S. Cl. ..................... 106/695; 106/35; 433/228.1; 623/23.62; 623/23.56; 501/134; 501/135; 501/136; 501/137; 501/124; 501/127; 501/153

(58) Field of Classification Search ............. 106/35, 106/695; 623/23.62, 23.56; 433/288.1; 501/134, 135, 136, 137, 124, 127, 153

See application file for complete search history.

(56) References Cited

U.S. PATENT DOCUMENTS

5,306,673 A    4/1994 Hermansson et al.

FOREIGN PATENT DOCUMENTS

| SE | 463 493 | 12/1990 |
|---|---|---|
| WO | 90/11066 | 10/1990 |
| WO | 00/19965 | 4/2000 |
| WO | 00/21489 | 4/2000 |
| WO | WO 01/76534 | 10/2001 |
| WO | WO 01/76535 | 10/2001 |

OTHER PUBLICATIONS

Joon B. Park et al., *Biomaterials—An Introduction*, 1992, Chapter 5, "Metallic Implant Materials," pp. 79-115, and Chapter 7, "Polymeric Implant Materials," pp. 141-168.

A. Ravaglioli et al., *Bioceramics*, 1992, Chapter 6, "Materials for Surgical Use," pp. 100-193.

(Continued)

*Primary Examiner*—C. Melissa Koslow
(74) *Attorney, Agent, or Firm*—Young & Thompson

(57) ABSTRACT

A chemically bonded ceramic material based on calcium aluminate hydrate with additives of primarily calcium titanate, but also chemically similar compounds. The material is a biocompatible material for implants, particularly for orthopaedic and dental applications. The material possesses the properties required for an orthopaedic biocement. It cures through reaction with water and develops its strength within a short period of time, has good workability prior to curing, is shape stable, has a low heat generation during curing, and is friendly to adjacent tissues.

23 Claims, 2 Drawing Sheets

OTHER PUBLICATIONS

Peter C. Hewlett, ed., Lea's Chemistry of Cement and Concrete, 1998, Chapter 13, "Calcium Aluminate Cements," pp. 713-775.

Philippe Kopylov et al., "Norian SRS versus functional treatment in redisplaced distal radial fractures," Acta Orthop Scand, V. 70, 1999, pp. 1-7.

David Knaack et al., "Resorbable Calcium Phosphate Bone Substitute," J Biomed Mater Res (Appl Biomater), v. 43, 1998, pp. 399-409.

Bengt Sandén et al., "Hydroxyapatite coating enhances fixation of loaded pedicle screws: a mechanical in vivo study in sheep," Eur Spine J, V. 10, 2001, pp. 334-339.

S.F. Hulbert et al., "Potential of Ceramic Materials as Permanently Implantable Skeletal Prostheses," J. Biomed. Mater. Res., V. 4, 1970, pp. 433-456.

I. Odler, *Special Inorganic Cements*, 2000, pp. 173-204.

CERAMIC MATERIAL AND PROCESS FOR MANUFACTURING

THE FIELD OF THE INVENTION

The present invention relates to a ceramic material based on hydrated calcium aluminate, which is suitable for implantation, particularly in the fields of orthopaedics and odontology. The invention also pertains to products that at least in part have been made from the material.

BACKGROUND OF THE INVENTION

Biocements

Particularly within orthopaedics, there is a need for biomaterials that can be finished for final use in a clinical environment, i.e. compounds which can be finally shaped at the time of a surgical operation. After shaping, the material should harden, or cure either uncovered in the operating theatre or positioned in the body. There is no generally accepted name for this type of materials. The concept of bone cement generally applies to the established polymer based cements often used for the fixation of hip-implants in the femoral bone. Biocement is a more general word for workable biocompatible materials, which cure in-situ through chemical reactions, including the ceramic compounds, further described below.

PMMA Bone Cements

There is a number of commercially available orthopaedic cements. The most established are based on the polymer polymethylmethacrylate (PMMA). This group of bone cements is mainly used for anchoring hip-joint protheses in the femoral and pelvic bones, or for the corresponding anchoring of knee joints. A big brand name among PMMA bone cements is Palacos® from Merck.

PMMA based materials have penetrated into orthopaedics, mainly due to suitable mechanical properties, a high degree of workability before curing, and a practical curing time.

The mechanical properties of PMMA bone cements are characterised by a relatively high fracture toughness, a compressive strength (80–120 MPa) being equal to or slightly lower than that of a femoral bone (130–200 MPa), and a considerably lower elastic modulus than the latter; 1–3 GPa for the cement compared to 10–15 GPa for the femoral bone, see Table 1.

However, PMMA-based cements have poor biocompatibility. Tissue in-growth cannot be established. Since the polymerisation does not proceed to completion, the material tends to leak monomers, a component of recognised toxic character. Furthermore, during curing heat development is such that the temperature rises to levels (above 50° C.) that cause cell necrosis in adjacent tissues.

A further disadvantage with PMMA-based cements is the shrinkage that occurs during curing (approximately 2–5%). This impairs the mechanical anchoring in the adjacent bone and consequently the possibility of early loading of the fracture. Preferably, orthopaedic cements should expand slightly during curing, as will be discussed further below.

Ceramic Biocements

In addition to the polymer based bone cements, there is a number of chemically curing cements based on ceramic components. Ceramic biocements for orthopaedic applications are often based on calcium phosphate, calcium carbonate or calcium sulphate. Examples of ceramic biocements products are: Norian SRS®, Osteoset®, Proosteon® and Biobon®.

In general, ceramic cements are much more biocompatible than those of PMMA. However, they suffer from insufficient mechanical strength. The manufacturers of Norian® and Biobon® provide compressive strength values around 30 and 40 MPa, respectively, see e.g. Table 1, much lower values that for natural bone.

Norian SRS is described in "Norian SRS versus external fixation in redisplaced distal radial fractures—A randomized study in 40 patients", by P. Kopylov, K. Runnqvist, K. Jonsson and P. Aspenberg, Acta Orthop Scand, 1999; 70 (1) 1–5.

Information about Biobon is given in "Resorbable calcium phosphate bone substitute", by Knaack D, Goad M E P, Aiolova M, Rey Ch, Tofighi A, Chakravarthy P, Lee D D, J Biomed Mater Res (Applied Biomater) 1998; 43: 399–409.

Other Biomaterials

As for ceramics materials, special attention has been paid to various types of hydroxyapatites (or calcium phosphates), against which bone tissue regenerates excellently. Hydroxyapatites are also naturally occurring in bone tissue. The mineral part (bone contains about 68–70% of minerals) is mainly calcium phosphates substances, e.g. hydroxyapatite, $Ca_{10}(PO_4)_6(OH)_2$. Bone attachment to hydroxyapatite is described in B. Sandén, C. Olerud, S. Larsson, "Hydroxyapatite coating enhances fixation of loaded pedicle screws: a mechanical in vivo study in sheep", Eur Spine J (2001) 10: 334–339).

Hydroxyapatite and other calcium phosphates have too poor mechanical properties for dental and orthopaedic applications when used alone (see WO/11979).

Another, less spread biomaterial is calcium aluminate, a central component of the present invention. Calcium aluminate for medical applications is described e.g. in S. F. Hulbert, F. A. Young, R. S. Mathews, J. J. Klawitter, C. D. Talbert and F. H. Stelling, "Potential of Ceramic Materials as Permanently Implantable Skeleton Prostheses", J. Biomed. Mater.res, vol. 4, PP. 433–456 (1970).

Calcium aluminate has been explored as a tooth filling material, e.g. the product Doxadent® produced by Doxa Certex A B, see e.g. PCT/SE99/01729, "Sätt att framställa en kemiskt bunden keramisk produkt, samt produkt", 29 Sep. 1999; and PCT/SE99/01803, "Dimension stable binding agent systems", 08 Oct. 1999.

SE-463 493 discloses a chemically bound ceramic material comprising a first binding agent selected from the group comprising aluminates, silicates and phosphates. The material is achieved through a specified production technique involving pre-compaction of the ceramic body. In addition, the ceramic material may comprise an inert phase of hydroxyapatite or oxides of titanium, zirconium, zinc and aluminium. The reasons for these additives are strength and biocompatibility.

SUMMARY OF THE INVENTION

In view of the drawbacks associated with prior art materials there is a need for a biocompatible biocement which develops appropriate strength characteristics within a short period of time, has good workability, is shape stable, has a low heat generation during curing, is friendly to adjacent tissue and does not leak toxic substances.

The use of the inventive material is mainly for making implants, in particular for the orthopaedic and dental fields.

The present invention achieves this with a material and manufacturing process. The material is a chemically bonded ceramic material, comprising 50–99 wt. % of a binding phase system based on partially or fully hydrated calcium aluminate, 1–50 wt. % of an inert additive, which is a ternary oxide of the perovskite structure described by the formula $ABO_3$, where O is oxygen and A and B are metals, and wherein the amount of the inert additive is equal to or less than the amount of said binding phase. The manufacturing process is a method for manufacturing the above identified ceramic material, comprising the steps of preparing a slurry comprising calcium aluminate, inert additives and a curing agent, and curing the slurry. Preferred embodiments are that the composition further comprises hydroxyapatite in an amount 0–50 wt. % of the amount of binding phase. In addition, the ceramic material has a compressive strength of at least 100 MPa and a hardness of at least 80 Vickers. As to the method, preferred embodiments are that the expansion during curing of the material is $\leq 0.8\%$. Moreover, during the processing, the temperature of the material preferably does not increase to more than 40° C. when cured in a living human body. An additive can also be added during the process as a water reducing agent based on the compounds polycarboxylic acids or polyacrylic acids, or a superplasticiser. The process and composition can preferably be used to produced a bone implant, tooth filling implant, and biocement.

BRIEF DESCRIPTION OF THE DRAWINGS

The present invention will now become more fully understood from the detailed description given herein, wherein reference is made to the accompanying figures, in which.

DETAILED DESCRIPTION OF THE EMBODIMENTS

Figure 1:
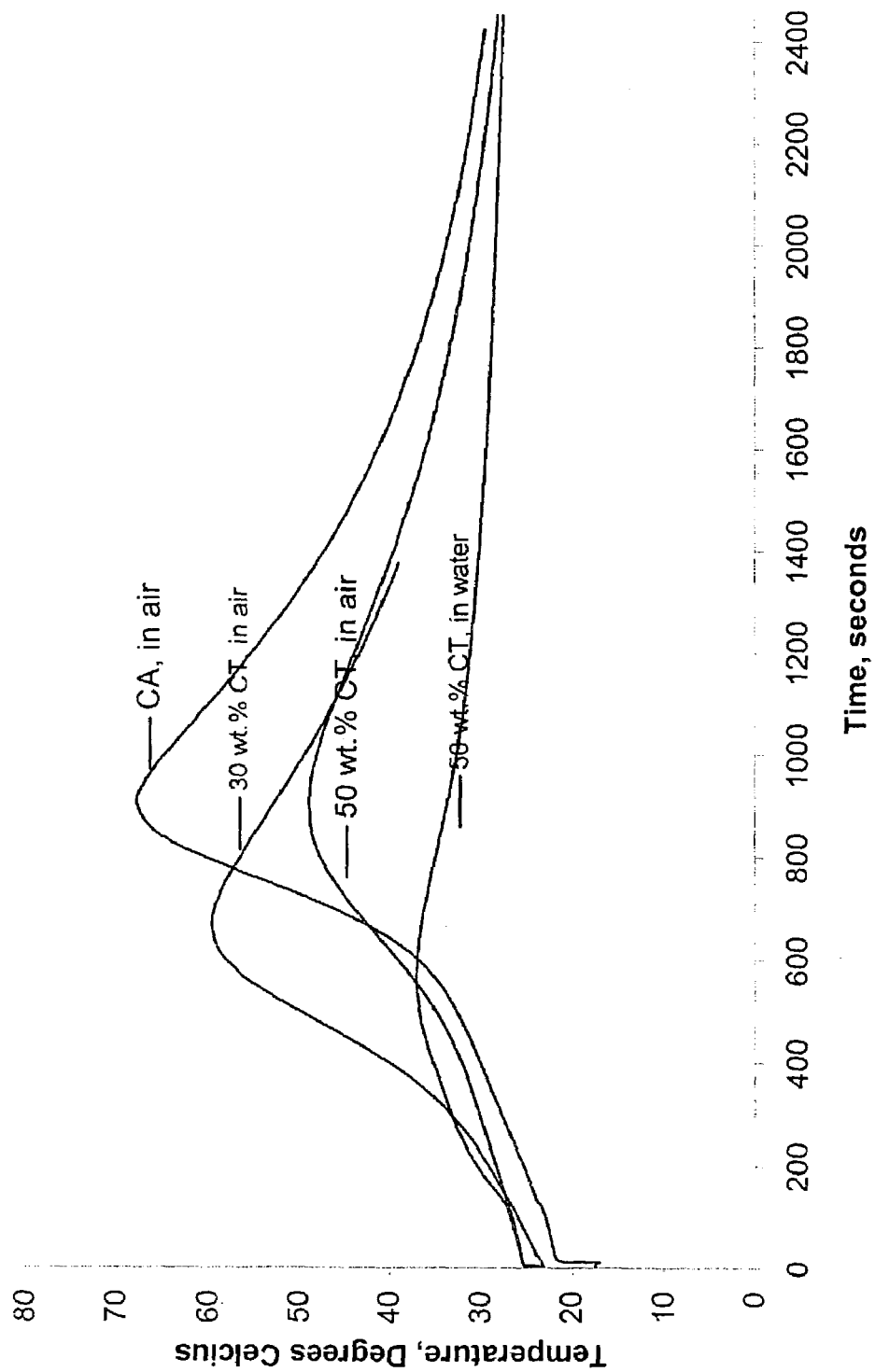
FIG. 1 shows a graph of the temperature development as a function of curing time for calcium aluminate (CA) with 0, 30 or 50 wt. % of calcium titanate (CT). The material without CT is for reference purposes, the other represent materials of the invention. The curing is performed in air or in water. The water to cement (w/c) ratio is 0.5 for all materials.

The present invention pertains to a chemically bonded ceramic material, which in particular is designed for orthopaedic implant applications. It also suits for dental applications. The material of the invention possesses the required properties of a biocement, being suitable for use as a fracture support material, for bone reinforcement of patients suffering of osteoporosis, and for fastening (anchoring) of implants in the skeleton. To suit these types of applications, the material fulfils the requirement profile given below.

Requirement Profile for an Orthopaedic Biocement

Mechanical Strength

The mechanical strength of a biocement should allow normal loading of the region affected by the implantation. For orthopaedic applications the strength should not deviate substantially from the natural bone. Excessive rigidity of implants, may focus stresses to regions adjacent to the implant.

The strength of natural bone varies considerably with the type of bone, its composition and age. The compressive strength of the strong outer (cortical) bone of a thighbone (femur) is typically about 150 MPa, while the spongier inner bone can exhibit a compressive strength below 10 MPa. In Table 1, typical mechanical property values of an entire human thighbone are given. Data is also included for PMMA-based bone cement, the ceramic biocement Norian SRS, and hydrated calcium aluminate, CAH, the base material of the present invention.

TABLE 1

Mechanical properties of human femoral bone and some orthopaedic materials: PMMA–based bone cement, the product Norian SRS and hydrated calcium aluminate (CAH).

| Property | Thighbone (femur) | PMMA (bone cement) | Norian SRS | CAH |
| --- | --- | --- | --- | --- |
| Density, g/cm$^3$ | 1.6–1.7 | 1.1–1.2 | 2.0–2.5 | 2.2–2.5 |
| Youngs modulus, GPa | 10–15 | 1–3 | 20–30 | 10–20 |
| Tensile strength, MPa | 90–130 | 30–70 | 5–7 | 10–20 |
| Compressive str., MPa | 130–200 | 80–120 | 20–30 | 100–250 |
| Fracture strain, % | 1–3 | 0.1–0.3 | 0.1–1 | 0.5–1 |
| Toughness, MPa · m$^{1/2}$ | 1–2 | 1–3 | 0.06–0.14 | 0.5–2 |
| Hardness (Vickers) | 50–100 | 50–100 | 10–20 | 50–100 |

For an orthopaedic implant material the mechanical strength should develop relatively fast, within a couple of hours, to enable early loading of the implant. Rapid development of the strength and early fixation of the implant is of great importance to enable early loading of the treated region. This speeds up the healing process and shortens the convalescence time.

Workability

Special requirements are set on the workability of a biocement. Before curing it should be possible to shape the material to conform to a cavity of arbitrary geometry. It should be possible to position the material by injection, with minimal surgical operation. The high degree of workability should remain for about 10 to 30 minutes, whereafter the material should cure.

Dimensional Stability

Dimensional stability, i.e. the degree of expansion or shrink occurring during curing, is crucial for a biocement. Shape alterations arise from chemical transformation of the curing process. For orthopaedic applications, a slight expansion during curing is most advantageous.

An expansion improves anchoring of the cement in the trabecular (cell) structure of the adjacent bone, thereby enabling higher and earlier loading of the implant. An expansion also drives accumulated body fluids out from the zone between implant and natural bone, thus promoting the establishment of a direct mechanical contact between implant and bone tissue. It is very disadvantageous if the cement material shrinks during or after curing.

However, to avoid the risk of cracks being developed as a result of internal tensions, there is also an upper limit for the degree of expansion that is acceptable. For a ceramic, the expansion should not exceed 1%, corresponding to the fracture tension of the material. Therefore, an expansion of 0.5 to 0.8% is optimal for a ceramic biocement. However, when used a tooth filling material, an expansion below 0.3% is required to avoid cracking of the tooth.

This expansion properties of a tooth filling material is described in PCT/SE99/01803, "Dimension stable binding agent systems", 08 Nov. 1999. This patent application also describes how the expansion of a calcium aluminate based binding system is controlled with small amount of additives. These additives may also be used to control the expansion of the material of the present invention.

Temperature Increase

To avoid adverse effects of the heat produced during curing of a biocement on adjacent tissues, the temperature should be kept below 40° C. Tissue death, necrosis, can occur at temperatures from about 50° C. Hence, a biocement curing through an exothermic reaction, should generate little heat, spread the heat generation over time, and dissipate the heat from the implant to the surrounding tissues as effectively as possible.

Biocompatibility

The biocompatibility is of fundamental importance to all implant materials. For orthopaedic applications, the natural regeneration of bone should be able to continue adjacent to the implant surface. A biocement should be chemically stable in tissue environments and contain biologically acceptable substances. Leakage of toxic substances and activation of allergic reactions should be avoided. Certain materials, e.g. titanium and hydroxyapatites, are recognised as being particularly biocompatible and are well established within the field of orthopaedics and odontology. Hydroxyapatites show particularly good characteristics in contact with bone.

Throughout this application the term biocompatibility is used a number of times implying certain properties on the material or surface in question. It should be noted that biocompatibility is used as a generic term for the different properties that are required or desirable for materials that are to be in contact with biological tissue.

Calcium Aluminates

The basic substance of the inventive material is a ceramic and consists mainly of phases of the ternary oxide system $CaO.Al_2O_3$, so called calcium aluminates. A number of stoichiometries exist for the system. Commercially available powders consist mainly of CA or $CA_2$, where C stands for CaO and A for $Al_2O_3$, according to accepted cement chemistry notations. $C_{12}A_7$ and $CA_6$ and $C_3A$ are phases that also have been described previously in the literature. All phases are applicable on the present invention.

Calcium aluminates are commercially available as powders with relative good purity, for example as the products Secar or Ternal White from LaFarge Aluminates. These products consist mainly of the phases CA or $CA_2$.

If a powder of calcium aluminate is mixed with a water-based solution, a hardening or curing process starts. It occurs due to a chemical reaction between the calcium aluminate grains and the water, a so-called hydration. During curing, a new binding phase is developed, consisting of calcium aluminate hydrates. The hydrates are developed through precipitation of hydrate crystallites from the liquid phase.

The initially formed hydrates are transformed, in several steps, into more stable phases of hydrates, following the chemical reactions provided below. The rate at which the transformation of hydrates takes place depends on temperature and additives. At room temperature the initial hydrate phase is $CaO.Al_2O_3.10H_2O$, typically abbreviated as $CAH_{10}$ (C=CaO, Al=$Al_2O_3$, H=$H_2O$). In this phase one unit of CaO and one unit of $Al_2O_3$ binds ten units of water. As will be seen below, the most stable phase is $C_3H_6$, which contains less water than $CAH_{10}$.

The following reactions for the hydration have been identified:

$$CA+10H \rightarrow CAH_{10}$$

$$2CA+11H \rightarrow C_2AH_8+AH_3$$

$$3CA+12H \rightarrow C_3AH_6+2AH_3$$

$$2CAH_{10} \rightarrow C_2AH_8+AH_3+9H$$

$$3C_2AH_8 \rightarrow 2C_3AH_6+AH_3+9H$$

All reaction steps are exothermic and heat is developed. Free water, $H_2O$, is formed in some of the reactions. This water can participate in the hydration of other, not yet hydrated calcium aluminate crystallites. In addition, the phase $AH_3$ ($Al(OH)_3$), an aluminium hydrate, is formed during the transformation of hydrates. This is the chemically least stable water-binding phase.

Binding phase systems based on hydrated calcium aluminate have unique properties. In comparison to other water binding systems, for example silicates, carbonates and sulphates of calcium, the aluminates are characterised by high chemical resistance, high strength and a relatively rapid curing. Due to these properties, CA-cements are used as construction materials in particularly tough environments involving elevated temperatures and corrosion.

The high strength of calcium aluminate cements is due to the high absorption capacity of hydrated water, which in turn results in a low residual water contents and low porosity. The high compaction also increases the resistance to corrosion.

Among hydrating binding phase systems, calcium aluminate has thus essential advantages as an implant material. The material cures through reaction with water, which implies that the curing process is not disturbed by water-based body fluids. Before curing, the material is well workable; it can be used both as slurry or paste. In the cured condition the material possesses a unique combination of chemical inertness and mechanical strength, as compared to other hydrating compounds.

In the invention, calcium aluminate is used as a binding phase in a composition, which, through the addition of selected non-hydrating inert phases, has been optimised in view of the properties required of an orthopaedic biocement, as described above.

Of particular interest for biomaterials containing calcium aluminate, are possibilities to reduce the aluminium content and the risk of aluminium leakage. Although negative effects of aluminium on tissues, have only been found for very high concentrations of ionic aluminium, it is still desirable to replace the aluminium with well established and biofriendly metals, such as titanium.

The risk of aluminium leakage, which is mainly to be related to the stages before the curing reactions are completed, is low and can be further reduced in two ways. One is by reducing the total amount of aluminium in the material, and the other is by suppressing the formation of the $AH_3$ phase, being the chemically least stable phase formed during hydration of calcium aluminate.

Material Compositions According to the Invention

In the present invention, compositions are sought that provide the properties, which are desired for an orthopaedic biocement. Of particular interest are improved mechanical properties, controlled temperature generation during curing, controlled expansion, increased biocompatibility, and reduced aluminium content.

Experiments show that the compound calcium titanate (CT) functions surprisingly well as an additive to CA in amounts of up to 50 wt. %. As illustrated in the examples below, addition of CT to CA provide improved strength and hardness to the material.

Experiments also show that with the addition of CT, both the transition of the hydrates to the stable $C_3AH_6$-phase, as well as the formation of the $AH_3$-phase are suppressed, compared to pure a reference sample of pure CA. This reduces the risk for Al-leakage and is advantageous for the mechanical properties.

Due to the relatively high amounts of inert phase, the temperature generation during curing is damped. Furthermore, aluminium is replaced by titanium in the structure. Further still, the calcium titanate does not affect the expansion properties of the base material. Therefore the expansion can be controlled by use of the same additives as described in PCT/SE99/01803, "Dimension stable binding agent systems", 08 Nov. 1999.

Calcium titanate (CT) is a naturally occurring mineral oxide compound with the stoichiometry $CaO.TiO_2$ ($CaTiO_3$), and a perovskite crystal structure. Calcium titanate shares the perovskite structure with several other ternary metal oxides of the type $ABO_3$. Here O is oxygen and A and B are positive ions of metals. The structure is cubic with A centrally placed in the unity cell, surrounded by 12 O-atoms and 8 B-atoms placed in the corners of the cell.

The atom A can be any of the metals Mg, Ca, Sr or Ba, all from Group 2 in the periodic table. The atom B, being Ti, Zr or Hf, is found in Group 4. All of these perovskite ternary oxides have similar physical properties and are relevant for the invention, as well as the combinations thereof.

One reason to replace calcium titanate with compounds of heavier elements than Ca and Ti, is to increase the X-ray opacity of the material, making implants more visible under the type of X-ray examination frequently used in hospitals.

Experiments also show, that inert phases of up to 50 wt. % of the ternary oxide system hydroxyapatite $Ca_{10}(PO_4)_6 \cdot (OH)_2$, can be added to CA with maintained, or even improved mechanical properties. This is of particular importance to the invention since hydroxyapatites are recognised bioceramics, particularly in bone contact.

Materials containing hydroxyapatite are known. A sintered ceramic material with hydroxyapatite is described in the patent WO 90/11979, "Composite Ceramic Material and Method to Manufacture the Material". The possibility of adding hydroxyapatite to a hydrating binding phase (which could be e.g. calcium aluminate) is described in the patent SE-463 493, "Sätt vid framställning av en kemiskt bunden keramisk produkt samt enligt sättet framställd produkt".

Preparation

The material of the invention is prepared with a process according to the following steps described below.

The starting point is a binding phase system based on calcium aluminates in powder form. The powder may consist of the more frequent phases CA or $CA_2$, but also the phases $C_{12}A_7$, $CA_6$ or $C_3A$ may be used. The powders are ground to a desired granulate size, for example with a ball mill. Granulate sizes below 10 μm have been found functional, but also larger grains can be explored.

Contaminations, that may affect the curing or the mechanical properties of the material, must be removed. Organic contaminations may be removed by heating the powder in air in a furnace at temperatures of 300–400° C.

To the calcium aluminate powder, the inert phase ceramic components are added as fine grained powders. Experiments show that amounts of up to 50 wt. % of ceramic may be used. Also for the inert phase powders, suitable grain sizes are below 10 μm. Specific for the invention are ternary oxide phases of the above described perovskite type, in particular those of calcium titanates, but also oxides of the general type $ABO_3$, where O is oxygen, A is Mg, Ca, Sr or Ba, and B is Ti, Zr or Hf.

A biocement as described above may also be the basis of a composite containing hydroxyapatit. In such a composite the biocement functions as a matrix holding the hydroxyapatit. To make such a composite, powders of hydroxyapatite (or calcium phosphates) in amounts of up to 50 wt. % may be added to the ceramic material.

Furthermore, dimension controlling phases, primarily calcium silicates and fumed silica (very finely grained silica), may be added. The function of such additives is to control the expansion occurring during curing, suitably such that the expansion is about 0.5–0.8% for orthopaedic applications or 0.3% for dental filling applications. The expansion controlling additives are described in the patent application PCT/SE99/01803, "Dimension stable binding agent systems".

Curing is achieved by adding a water solution with suitable additives (not specific of the present invention). The rate of curing is controlled by the addition of various salts, primarily lithium chloride, LiCl, as described in I. Odler, "Special Inorganic Cements", (2000) 173–204.

Other additives may be used to control the viscosity or workability. Most preferred are organic polymers providing dispersion effects. These may e.g. be varieties of polycarboxylic acids or polyacrylic acids.

The water solution is added and well mixed with the powder in such amounts that, the ratio of the amount of water to the amount of hydrating phase (the water to cement ratio, w/c-ratio) is controlled. Suitable w/c-ratios are 0.2 to 0.4. After shaping, the powder-liquid mix is left to cure.

Advantages with the Material According to the Invention

It has been shown that additions of calcium titanate (CT) to calcium aluminate (CA) results in materials having the following advantages as a biocement for orthopaedic applications:

By the addition of CT, a substantial part of the aluminium in the ceramic is replaced by titanium. In this way, the risk of aluminium leakage is reduced; partly because the amount of aluminium present is reduced, and also because CT, during an initial stage, reduces the extent of formation of the $AH_3$-phase. Titanium is also recognised for its biocompatibility.

Experiments unexpectedly showed that CT can be added in amounts of up to 50% to CA without reducing the mechanical properties of the cured material. In fact, experiments show better strength for materials with CT than without.

The addition of CT can also be used without affecting the expansion properties of CA. Experiments show that CA/CT-mixtures with up to 50-wt. % CT in CA have essentially the same expansion as pure CA. The expansion can be controlled to desired values of 0.3–0.8 with additives, as described above.

The material of the invention may also be implemented as layers or coatings on substrates of other materials, e.g. metals, polymers or other ceramics. Coatings based on CA are described in our co-pending Swedish patent application SE-0104440-3

EXAMPLES

Experimental examples will now illustrate the method of producing the material of to the present invention and the properties of the material. These should not be construed as limiting to the scope of the invention.

Example 1

This example describes the manufacturing procedure of ceramic materials consisting of hydrated calcium aluminate with various amounts of calcium titanate, and the mechanical properties of these materials.

As raw material, the commercial product Ternal White® from Lafarge Aluminates, was selected. This is a calcium aluminate with an $Al_2O_3/CaO$-ratio of about 70/30. However, any other similar calcium aluminate powder would lead to similar results.

The grain size of this powder was reduced my ball milling. The milling reduced the size of 90% of the grains to less than 10 µm.

The milling was performed with a rotating cylindrical plastic container filled with ⅓ of its volume with powder, and about ⅓ of its volume with inert silicon nitride milling spheres having a diameter of about 10 mm. The milling liquid was iso-propanol. The total milling time was 3 days.

After milling, the milling bodies were removed by sieving and the alcohol was evaporated. Thereafter the milled powder was burnt at 400° C. for 4 hours, to remove any rest water and residual organic contamination.

Titanate powder from the Aldrich Chemical Company (purity 99%), having a similar or smaller grain size than that of the calcium aluminate, was added to the powder. Calcium titanate powder was added in proportions of 30, 40, and 50% in weight to the milled Ternal White® powder.

The powder mix and water based solution made from de-ionised water, were mixed in such proportions that the ratio of the amount of water to the amount of milled Ternal White® powder (the w/c-ratio) was kept constant at 0.25, 0.30 or 0.50, as related to the powder weight.

Prior to mixing water and powder, some agents were added to the water. To accelerate the curing process, 0.1 wt. % of the accelerator LiCl was added. An increased flowability of the slurry was achieved by adding 1 wt. % of an agent that reduces the amount of water necessary to keep a high flowability (referred to below as a water reducing agent). The agent reducing the amount of water was selected from a group of highly efficient water reducing agents called superplasticisers, e.g. the commercial product Conpac 30® from Perstorp AB, but any other similar agent would also function. The effects of these additives (accelerators and water reducing agents) are known within the field.

The powder-liquid mixtures were left to cure in plastic containers in a humid environment, i.e. saturated with water, at 37° C. Each container held about 10 g of material.

The effects of curing time and composition on the hardness and strength are presented in Table 2. As can be seen, positive effects on the hardness and strength is achieved by the addition of CT. The mechanical properties increase during the first 4 weeks. This initial increase in hardness/strength is a known phenomenon.

TABLE 2

Mechanical properties of some calcium aluminate and calcium titanate (CA and CT) compositions, cured in saturated humidity at 37° C.

| Material compositions and curing times | Hardness, HV w/c = 0.50 | Hardness, HV w/c = 0.25 | Bending strength, MPa w/c = 0.30 |
|---|---|---|---|
| CA, 24 hrs | 35–45 | 60–70 | 6–8 |
| CA + 30% CT, 24 hrs | 40–50 | 65–75 | 6–10 |
| CA + 50% CT, 24 hrs | 45–55 | 70–75 | 8–10 |
| CA, 4 weeks | 50–60 | 90–110 | 14–18 |
| CA + 30% CT, 4 weeks | 55–65 | 100–110 | 16–20 |
| CA + 50% CT, 4 weeks | 60–70 | 105–115 | 16–20 |

Example 2

This example describes materials of hydrated CA with various amounts of calcium phosphate, and their mechanical properties.

CA powder of the type Ternal White from Lafarge Aluminates was prepared following the same procedure as in Example 1.

To this powder, a calcium phosphate powder ($Ca_5(PO_4)_3$OH) from the company Carl Roth GmbH+Co Karlsruhe, with a similar grain size as the CA, was added in proportions of 10, 20 and 50 wt. %. A similarly prepared CA without phosphate additives was used as reference. The same agents as in example 1 were added to the water. The w/c-ratio was set to 0.4, as related to the powder weight.

As in example 1, the powder-water mixtures were cured in containers holding about 10 g of material, in an environment saturated with water, at 37° C.

The hardness results are presented in table 3. As can be seen, a positive effect on the hardness of the calcium phosphate additive is achieved after two weeks of curing. Additions of calcium phosphate increased the hardness.

TABLE 3

Vickers hardness of some calcium aluminate and calcium phosphate (CA and CP) compositions, cured in saturated humidity at 37° C.

| Material compositions and curing times | Hardness, HV w/c = 0.40 |
|---|---|
| CA, 24 hrs | 30–40 |
| CA + 10% CP, 24 hrs | 35–40 |
| CA + 20% CP, 24 hrs | 35–40 |
| CA + 50% CP, 24 hrs | 35–40 |
| CA, 2 weeks | 55–65 |
| CA + 10% CP, 2 weeks | 75–85 |
| CA + 20% CP, 2 weeks | 90–100 |
| CA + 50% CP, 2 weeks | 90–100 |

Example 3

This example serves to illustrate that an addition of calcium titanate, CT, can be used to reduce the temperature generation during curing of CA. CA powder of the type Ternal White from Lafarge Aluminates was prepared following the same procedure as in Example 1. Powder mixtures with 30 wt. % and 50 wt. % of titanate were prepared as well.

The powder mixtures are mixed with de-ionised water, keeping the ratio of the weight of the water to the weight of the CA powder constant at 0.5.

For all powder mixtures, an accelerator in the form of the Li-salt, LiCl was added to the de-ionised water. This increased the curing time to about 10 minutes. To illustrate the effect of the surrounding medium, the curing was performed in air and in water.

The water-powder mixtures are cured in plastic containers, each holding about 10 g of the mixtures. During curing of the ceramics, the temperature in the centre of the ceramic bodies was measured with a thermocouple. The development of the temperature over time for CA with 0, 30 or 50 wt. % of CT is presented in FIG. 1. The curing time is counted from the start of the rapid temperature increase to the time when the temperature peaks.

As can be seen in FIG. 1, the temperature falls below 40° C. for compounds with 50 wt. % CT cured in a humid environment, when the curing time is in the order of 10 minutes.

Example 4

This example serves to describe the effect of the generation of phases caused by the addition calcium titanate, CT.

Calcium aluminate powder of the type Ternal White from Lafarge Aluminates was prepared following the same procedure as in Example 1. A powder mixture with 50 wt. % CT was also prepared as in example 1. The water to cement (w/c) ratio is 0.5 both materials.

Figure 2:
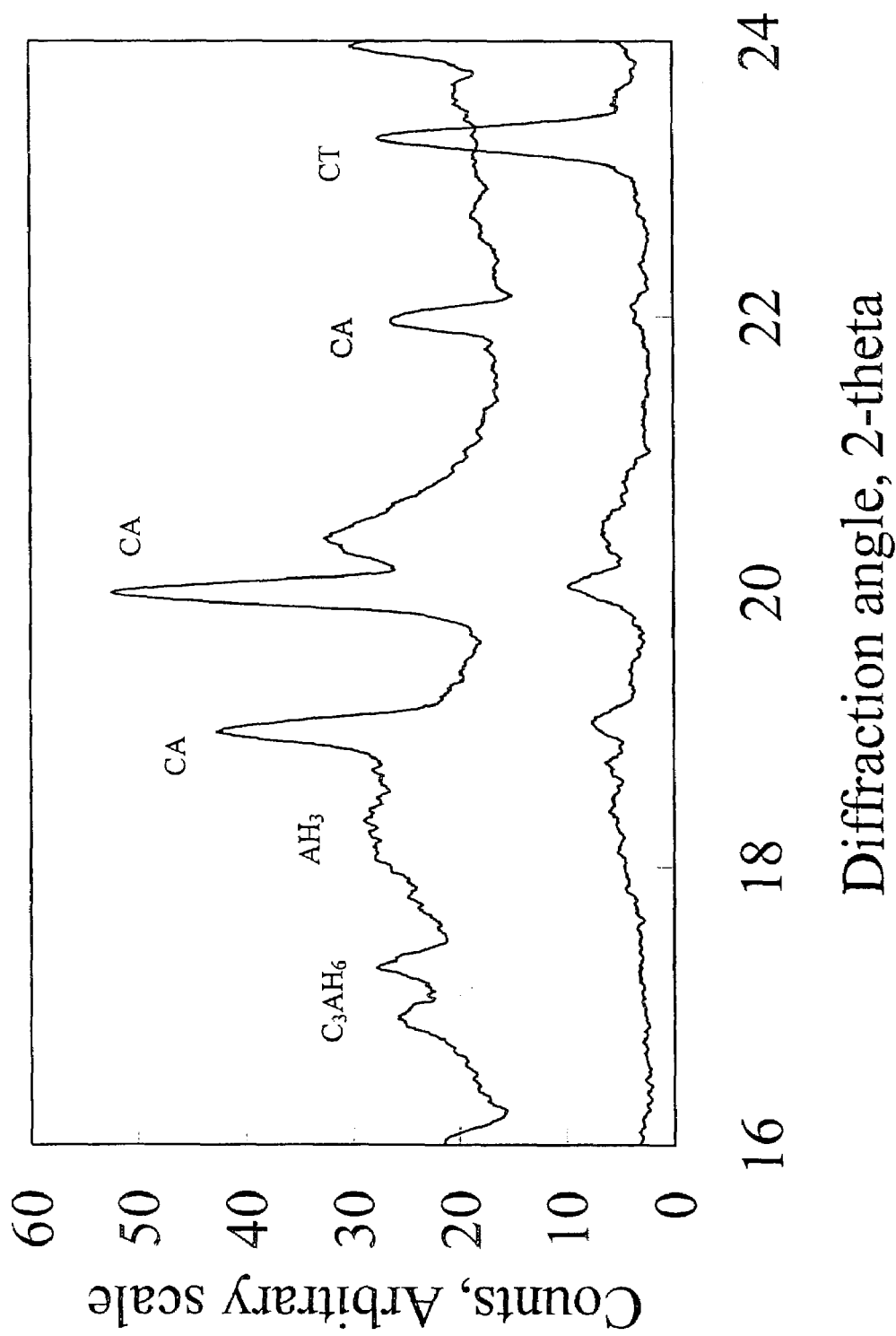
FIG. 2 shows an X-ray diffractogram describing the development of different phases of the present invention material. The upper curve is from a calciumaluminate sample and the bottom curve is made form a calciumaluminate with 50 wt. % calcium titanate after 4 weeks of curing at room temperature. The water to cement (w/c) ratio is 0.5 both materials.

De-ionised water was added to the powder mixtures, keeping the ratio of the w/c-ratio at 0.5. No accelerator or dispersion agents were used. The phase composition after 4 weeks of curing is presented in the diffractogram in FIG. 2. The upper curve is from a CA sample and the bottom curve is made form a CA with 50 wt. % CT after 4 weeks of curing at room temperature.

The diffractogram illustrates that for the CA+CT material, the transition to the weaker $C_3AH_6$-phase has not yet occurred, and that the $AH_3$-phase is suppressed, compared to the pure CA-material.

It should be understood that the detailed description and specific examples, while indicating preferred embodiments of the invention are given by way of example only.

Various changes and modifications within the spirit and scope of the invention will become apparent to those skilled in the art from this detailed description.

The invention claimed is:

1. Chemically bonded ceramic material, comprising:
   50–99 wt. % of a binding phase system based on partially or fully hydrated calcium aluminate,
   1–50 wt. % of an inert additive, which is a ternary oxide of the perovskite structure described by the formula $ABO_3$, where O is oxygen and A and B are metals, and
   wherein the amount of the inert additive is equal to or less than the amount of said binding phase.

2. Ceramic material according to claim 1, wherein A in the perovskite structure is selected from the group comprised of Mg, Ca, Sr or Ba, and that the B in the perovskite structure is selected from the group comprised of Ti, Zr, or Hf.

3. Ceramic material according to claim 1, wherein the inert additive comprises mixtures of two or more of the ternary oxides.

4. Ceramic material according to claim 1, further comprising hydroxyapatite in an amount 0–50 wt. % of the amount of binding phase.

5. Ceramic material according to claim 1, wherein further comprising calcium silicates and/or fumed silica.

6. Ceramic material according to claim 5, wherein the expansion during curing of the material is $\leq 0.8\%$.

7. Ceramic material according to claim 1, wherein the material has a compressive strength of at least 100 MPa.

8. Ceramic material according to claim 1, wherein the material has a hardness of at least 80 Vickers.

9. Method for manufacturing a ceramic material that has 50–99 wt. % of a binding phase system based on partially or fully hydrated calcium aluminate, 1–50 wt. % of an inert additive, which is a ternary oxide of the perovskite structure described by the formula $ABO_3$, where O is oxygen and A and B are metals, and wherein the amount of the inert additive is equal to or less than the amount of said binding phase, the method comprising the steps of:
   preparing a slurry comprising calcium aluminate, inert additives and a curing agent, and
   curing said slurry.

10. Method according to claim 9, wherein the slurry is cured in a humid environment.

11. Method according to claim 9, wherein the temperature of the material does not increase to more than 40° C. when cured in a living human body.

12. Method according to claim 9, wherein the curing agent is water, optionally with additives for accelerating curing.

13. Method according to claim 12, wherein the additive is lithium chloride, LiCl, acting as a curing accelerator.

14. Method according to claim 10, further comprising an additive as a water reducing agent based on the compounds polycarboxylic acids or polyacrylic acids, or a superplasticiser.

15. Bone implant comprising the ceramic material defined in claim 1.

16. Tooth filling implant comprising the ceramic material defined in claim 1.

17. Biocement comprising the ceramic material defined in claim 1.

18. Ceramic powder composition, comprising:
   50–99 wt. % of a binding phase system based on calcium aluminate,
   1–50 wt. % in volume of an inert additive, which is a ternary oxide of the perovskite structure described by the formula $ABO_3$, where O is oxygen and A and B are metals, and
   wherein the amount of the inert additive is equal to or less than the amount of said binding phase.

19. Ceramic powder composition according to claim 18, wherein A in the perovskite structure is selected from the group consisting of Mg, Ca, Sr and Ba, and B in the perovskite structure is selected from the group selected from the group consisting of Ti, Zr, and Hf.

20. Ceramic powder composition according to claim 18, wherein the inert additive comprises mixtures of two or more of the ternary oxides.

21. Ceramic powder composition according to claim 18, wherein said composition further comprises hydroxyapatite in an amount 0–50 wt. % of the amount of binding phase.

22. Ceramic powder composition according to claim 18, wherein the grain size of the powder particles is smaller than 10 µm.

23. Ceramic powder composition according to claim 18, wherein said composition further comprises calcium silicates and/or fumed silica.

* * * * *